United States Patent
Kyriakou

(10) Patent No.: US 10,512,441 B2
(45) Date of Patent: Dec. 24, 2019

(54) COMPUTED TOMOGRAPHY HAVING MOTION COMPENSATION

(71) Applicant: SIEMENS AKTIENGESELLSCHAFT, München (DE)

(72) Inventor: Yiannis Kyriakou, Spardorf (DE)

(73) Assignee: Siemens Healthcare GmbH, Erlangen (DE)

( * ) Notice: Subject to any disclaimer, the term of this patent is extended or adjusted under 35 U.S.C. 154(b) by 743 days.

(21) Appl. No.: 14/914,467

(22) PCT Filed: Aug. 29, 2013

(86) PCT No.: PCT/EP2013/067911
§ 371 (c)(1),
(2) Date: Feb. 25, 2016

(87) PCT Pub. No.: WO2015/028069
PCT Pub. Date: Mar. 5, 2015

(65) Prior Publication Data
US 2016/0206272 A1   Jul. 21, 2016

(51) Int. Cl.
*A61B 6/00*   (2006.01)
*A61B 6/03*   (2006.01)

(52) U.S. Cl.
CPC ............ *A61B 6/5264* (2013.01); *A61B 6/032* (2013.01); *A61B 6/582* (2013.01); *A61B 6/585* (2013.01)

(58) Field of Classification Search
None
See application file for complete search history.

(56) References Cited

U.S. PATENT DOCUMENTS

| | | |
|---|---|---|
| 5,579,359 A | 11/1996 | Toth |
| 2003/0142787 A1 | 7/2003 | Jabri et al. |

(Continued)

FOREIGN PATENT DOCUMENTS

| | | |
|---|---|---|
| CN | 102982510 A | 3/2013 |
| DE | 102011086771 A1 | 5/2013 |

(Continued)

OTHER PUBLICATIONS

Chinese Office Action for Chinese Application No. 201380079236.2, dated Feb. 26, 2018.

(Continued)

*Primary Examiner* — Matthew C Bella
*Assistant Examiner* — Brian D Shin
(74) *Attorney, Agent, or Firm* — Lempia Summerfield Katz, LLC

(57) ABSTRACT

The embodiments relate to a method for producing a digital volume model of a body volume by a sensor device, which sensor device includes a plurality of radiation sensors, of which each produces a pixel value in a projection. In order to produce the volume model, a plurality of projections from different projection angles (a) are produced and the volume model is computed from sensor positions of the radiation sensors and pixel values of the radiation sensors. For at least one projection angle (a), the sensor positions are corrected by a respective correction vector for rigid motion compensation. The problem addressed is that of also compensating the non-rigid motion of the body volume (i.e., the deformation) in the computation of the volume model. This problem is solved in that, in order to correct the sensor positions, the projection surface provided by the totality of the radiation sensors is divided into a plurality of sub-surfaces and a separate correction vector is determined for each of the sub-surfaces independently of each other.

20 Claims, 5 Drawing Sheets

(56) References Cited

U.S. PATENT DOCUMENTS

| | | |
|---|---|---|
| 2003/0167142 A1 | 9/2003 | Chell et al. |
| 2004/0260170 A1 | 12/2004 | Wood et al. |
| 2011/0158488 A1 | 6/2011 | Cohen et al. |
| 2012/0326034 A1 | 12/2012 | Sachs et al. |
| 2013/0129172 A1 | 5/2013 | Boese et al. |
| 2014/0226891 A1 | 8/2014 | Kunze et al. |

FOREIGN PATENT DOCUMENTS

| | | |
|---|---|---|
| DE | 102013202313 A1 | 8/2014 |
| EP | 1346689 A3 | 12/2003 |

OTHER PUBLICATIONS

Kyriakou, Y., et al. "Simultaneous misalignment correction for approximate circular cone-beam computed tomography." Physics in medicine and biology 53.22 (2008): 6267.

Neukirchen, Christoph, Marco Giordano, and Steffen Wiesner. "An iterative method for tomographic x-ray perfusion estimation in a decomposition model-based approach." Medical physics 37.12 (2010): 6125-6141.

PCT International Search Report and Written Opinion of the International Searching Authority dated Nov. 18, 2013, for corresponding PCT/EP2013/067911.

COMPUTED TOMOGRAPHY HAVING MOTION COMPENSATION

RELATED CASES

The present patent document is a § 371 nationalization of PCT Application Serial Number PCT/EP2013/067911, filed Aug. 29, 2013, designating the United States, which is hereby incorporated by reference.

BACKGROUND

The present embodiments relate to a tomography system and a method for generating a volume model of a body volume. The volume model can be used to generate, for example, a volume graphic of the body volume, that is to say for example of the interior of a patient's body. The volume model is formed on the basis of pixel values of a plurality of projections of the body volume, wherein the projections are generated on a projection surface from different projection angles. When computing the volume model from the projections, a motion performed by the body volume between the times of projection is compensated. The tomography system according to one embodiment may be designed, for example, as an X-ray-based computed tomography scanner.

In order to generate each projection, radiation, for example X-rays, is projected through the body volume, that is to say for example the patient, onto radiation sensors of a detector in the form of beam bundles. The totality of the beams typically defines a beam fan (e.g., conventional computed tomography (CT)) or a cone beam (cone beam CT). The projection surface in total is provided by the totality of the radiation sensors, that is to say the matrix of the radiation sensors. Each radiation sensor generates a pixel value. Each pixel thus represents an individual surface element of the projection surface. By rotating the radiation source and the detector with its projection surface, the body volume is transilluminated from different projection angles.

The computation of the volume model can be based on the reconstruction of the beam profile of the beams, with which the body volume is transilluminated. As known from computed tomography: at a specific projection angle, the beam profile is reconstructed starting from the position of each radiation sensor up to the radiation source.

By reconstructing the beam profiles for all pixel values of the projections and for all projection angles, the result for individual volume elements of the body volume is a value, for example, of the absorption property of the material located in the volume element with respect to the radiation used. Such a value that is associated with a volume element is also referred to as a voxel value (voxel–volume element). A suitable indicated value for absorption coefficients are Hounsfield units (HU). The collection of the volume elements and of the voxel values ascertained in relation thereto form the described digital volume model, which can be provided as a so-called 3D image data set. In humans or animals, the position and form of tissue, bones and organs can be deduced in a volume model.

In order to obtain projections from different projection angles, the detector and the radiation source are moved around the body volume along a prespecified trajectory. Typically, a rotational movement about a rotation center in which the body volume is arranged is performed. The trajectory can thus be a circular orbit or a helix. Here, the detector generally does not follow the planned trajectory exactly. Owing to deformations of the carrier structure of the detector, due to weight, it is possible for the sensor position of each radiation sensor to deviate. This deviation of the sensor position should be taken into account when reconstructing the beam profile, so that the correct pixel values are combined with one another when it comes to computing the absorption coefficients of a specific volume element.

To this end, the deviations of the actual trajectory of the detector and of the radiation source from the planned trajectory can be described as the relative movement between the focus (radiation source) and the detector, and it is possible correspondingly to define detector position vectors U and V as a description of the position of the projection plane in space and a source vector S for the position of the focus. For each projection angle, such vectors U, V, S are defined in order to correct the sensor position or the source position in the reconstructions of the beam profiles (i.e. match them to real situations). If the movement of the body volume is still detected in that case, for example by filming a patient in a computed tomography scanner with a camera and thus deriving his or her movement, it is possible to determine another object vector O for each projection angle in order to compensate also for this movement of the body volume in the reconstruction. In other words, it is possible to specify for each projection angle a perspective transformation matrix of 3×4 elements, which can be used as the basis for the reconstruction of a beam profile.

It is possible to indicate by the detector position vectors U, V how the detector is displaced relative to the constructively envisaged position of the detector, for example owing to the deformations of the carrier structure, once the detector has assumed a specific projection angle. It is likewise possible by way of the source vector S to describe the displacement of the radiation source relative to the constructively envisaged position of the source. The respective constructively envisaged position is obtained from the type of construction of the mechanical suspension of the detector with the radiation sensors and of the radiation source, that is to say for example from the design plan. By way of example, the detector position vectors U, V and the source vector $S$ can indicate that the detector is lower by one millimeter and the radiation source is tilted forward, for example by half a millimeter, in each case relative to the position that the detector and the radiation source would have in the case of an ideally rigid mechanical suspension.

So as to ascertain for each projection angle, the relative positional change of the detector (detector position vectors U, V) and of the radiation source (source vector S) with respect to one another, an off-line calibration measure can be used in which a phantom with a known geometry is recorded. However, special algorithms can also be used that can determine the geometry generally on the basis of image data of a patient (Y. Kyriakou et al., "Simultaneous misalignment correction for approximate circular cone-beam computed tomography," in: Physics in Medicine and Biology, 53, 6267, 2008). This algorithm, for example, is further developed in the embodiments.

A motion compensation can be carried out by the detector position vectors U, V, the object vector O and the source vector S. The motion correction has so far been rigid, that is to say only translational movements in one spatial direction by a corresponding displacement were compensated for by the stated correction vectors (i.e., factored out). This applies both to the object movement and to a displacement of the detector relative to the radiation source. The object is here considered as an ideally rigid body which does not deform during movement. On the basis of this assumption, all parts of the object always carry out a movement in the same direction.

What is not possible in the prior art is the compensation of flexible, non-rigid movements, that is to say deformations, of a body volume. However, these can be caused for example by breathing movements of a patient. Such non-rigid movements prevent a consistent image reconstruction.

SUMMARY AND DESCRIPTION

The scope of the present invention is defined solely by the appended claims and is not affected to any degree by the statements within this summary.

The present embodiments are based on the object of compensating for non-rigid movements during the computation of a volume model.

It is the case also in the method according to one embodiment that a volume model is computed on the basis of a plurality of projections which are generated at different projection angles. During the reconstruction of the beam profile, the sensor position of each beam sensor is corrected for at least one projection angle by at least one correction vector. As is known from the prior art, each correction vector is designed to describe or to compensate for the deviation of the position of the projection surface from the planned movement trajectory. What is achieved in a known manner by way of the correction vectors is that a volume model is generated on the basis of the corrected sensor position, which volume model meets a predetermined optimization criterion. The image properties are thus improved with respect to a volume model computed from non-corrected sensor positions (i.e., for example the imaging distortion is reduced).

According to the prior art, the position of the projection surface overall is displaced by the described detector position vectors U and V at a given projection angle (i.e., a rigid movement is recreated). According to the present embodiment, provision is instead made here for in each case the projection surface to be divided into a plurality of partial surfaces for one or more or all of the projection angles, and for in each case a dedicated correction vector to be ascertained relating to the partial surfaces independently from one another. Thus, there is not only one correction vector U, V per projection angle, but a plurality of correction vectors $u_1$, $u_2$ to $u_n$ and $v_1$, $v_2$ to $v_n$, n being the total number of partial surfaces. Each partial surface can here include one or more pixels. In other words, the partial surfaces thus represent segments of the projection surface. The partial surfaces can be, for example, in the form of tiles, that is to say rectangular.

The correction vectors can be added to the coordinates known from the design plan of the tomography system, that is to describe in each case a projection angle-dependent positional change, or be defined as absolute position vectors with projection angle-dependent coordinates. The vectors are here referred to as correction vectors in both cases. In connection with the embodiments, a correction vector is generally understood to mean an indication relating to a spatial displacement of the associated partial surface. The correction vectors are preferably 3D vectors. It is also possible for two correction vectors per partial surface to describe a displacement u in a first spatial direction and a further displacement v in a second spatial direction, u and v being able to be oriented for example orthogonally with respect to one another. The correction vectors can be used, for example, as the two known detector position vectors U and V in the method described in the introductory part.

By ascertaining for each partial surface a dedicated correction vector for a specific projection vector, it may be possible for the two partial surfaces to be displaced computationally with respect to one another owing to corresponding values of correction vectors of two or more partial surfaces. What this actually means is that the radiation sensors move with respect to one another. However, mechanically this is not possible since the radiation sensors are fixedly connected to one another within a detector. What is actually compensated for by this computational recreation of the relative movement of partial surfaces is a deformation of the body volume. That is to say, instead of recreating in a complex manner a soft, deformable body volume in the computation of the volume model, a rigid body volume is assumed and, for example, the deformation of an organ of a patient is modeled by movable partial surfaces of the projection surface that can be displaced with respect to one another. That is to say, overall independent sub-trajectories come about for the entire recording process during the movement of the projection surface about the body volume for the partial surfaces, which sub-trajectories are described by the correction vectors for each position angle and for each partial surface. In other words, distortions in the body volume are thus compensated for by way of a computational displacement of the partial surfaces with respect to one another. The displacement is preferably spatial. As a result, a large number of distortions can be compensated for successfully.

For the reconstruction of the beam profile from a specific radiation sensor, that is to say a specific pixel, up to the radiation source, the prior art generally uses filtered back projection that can be carried out by the known Feldkamp reconstruction (FDK) algorithm. However, the FDK algorithm can prove to be unsuitable if the projection surface, as is envisaged according to the embodiments, is divided into a plurality of partial surfaces. An advantageous development of the method according to one embodiment therefore makes provision for the volume model to be ascertained using an algebraic reconstruction technique (ART). An algebraic reconstruction technique is based on the approach of iteratively computing, for example, the absorption coefficients of the volume model and, to effect in each iteration step, a correction of an absorption coefficient in dependence on an improvement of one or more optimization criteria. As a result, in an ART, between each iteration the reconstruction result is compared to the measured data such that the consistency with respect to the data remains ensured even if the coordinates of the partial surfaces are displaced with respect to one another by the correction vectors, which after all do not correspond to the real arrangement of the radiation sensors.

One example of an ART algorithm is the method as per the publication of Neukirchen et al. (C. Neukirchen, M. Giordano, and S. Wiesner, "An iterative method for tomographic X-ray perfusion estimation in a decomposition model-based approach." Medical Physics, vol. 37, no. 12, pp. 6125-6141, December 2010). DE 10 2011 086 771 A1 likewise discloses an ART algorithm. The consideration of a temporal progression provided therein is not necessary in the present embodiments due to the motion compensation. It is generally also possible for another ART to be used, in particular one according to the Kaczmarz method.

The mentioned non-rigid movements, that is to say for example a deformation of an organ inside the body volume, are expressed in a computation of the volume model in unsharp, blurry regions, for example a smeared contour of an organ edge.

The correction vectors are preferably iteratively optimized. Once a volume model is computed, a non-rigid movement can be compensated for further by further changing the correction vectors and re-computing the volume model using the changed correction vectors.

Such a change or optimization of the correction vectors is ascertained according to one embodiment likewise with reference to an optimization criterion. What has proven particularly suitable here is an optimization criterion according to which an entropy value E is computed for the volume model on the basis of the voxel values of the initially computed volume model, that is to say for example the absorption coefficients of the individual volume elements. To this end, for example the following formula can be used as a basis:

$$E = \sum_{q=0}^{Q} (h(q) \log h(q)).$$

What is assumed here is that voxel values, such as the absorption coefficients, in the volume model have values in an interval from 0 to Q. In that case, all voxel values having a specific value q are counted in the volume model, which gives the absolute number H(q). The normalized histogram h(q)=H(q)/N is then computed therefrom, N being the total number of volume elements. If unsharp, blurred edges are present in the volume model, the entropy E of the volume model is greater than in the case of sharp edges. The aim here is to minimize the entropy E by changing the correction vectors.

To this end, in the method according to one embodiment, preferably a gradient descent method is used that is realized in particular with an adaptive increment size by changing a corresponding scaling constant c for each iteration step k. What has proven to be particularly simple for the gradient descent method realizable by the method is the Newton method. Here, the correction vectors to be optimized are combined into a total vector x. For an iteration from iteration step k to the subsequent iteration step k+1, the new correction vectors x(k+1) are:

$x(k+1)=x(k)+c(k)d(k).$

Added on to the vector x(k) is thus a scaled correction vector d(k) that is scaled using the scaling constant c(k), which describes the Newton direction for the correction. This correction addition comes about preferably as follows:

$d(k)=f''(x(k))^{-1}(-f'(x(k))).$

Here, f(x(k)) is the value of the cost function (for example the above entropy value E), as has been obtained with the correction vectors x(k). The computation rule for computing the cost function in dependence on the combined correction vectors x(k) should thus be derived once according to the equation for d(k) with respect to the vector values of the correction vectors x(k) such that f'(x(k)) is obtained, and then derived a second time, so that f''(x(k)) is obtained.

Since the computation rule for f(x(k)) can be very complex, the generally known secant method is used according to a preferred embodiment of the method to realize a particularly quick computation of the described first and second derivations.

In order to arrive at suitable correction vectors with as small a number of iteration steps as possible, and in particular to initialize the correction vectors with suitable initial values, an advantageous development of the method makes provision for a priori knowledge relating to the body volume of the object to be incorporated in the computation of the correction vectors. According to one embodiment of the method, in this respect the optimization criterion takes into consideration, at least in an initialization phase (which can comprise for example the first or the first two or the first five or the first ten iterations) in the computation of the correction vectors, that the volume model owing to the sensor positions described by the correction vectors is intended to deviate less from a specified predetermined volume model of the body volume according to a specified error quantifier than in the case of the use of non-corrected sensor positions. For example, with a previously ascertained CT data set (a statistical model of the object), an assumption relating to the object size and/or composition can be used as a basis as the predetermined volume model. The better the object is known, the better, more accurate and faster it is possible for the iterative optimization of the correction vectors to converge. For the error quantifier, for example, the sum of squared differences between the predetermined volume model and the computed volume model can be used as the basis. If, for example, the head of a patient is recreated by the volume model as the body volume, the elliptical profile of a head can be used as the basis as the predetermined volume model. If the result in that case owing to the current correction vectors is a non-elliptical volume model, this is reflected as a deviation from the elliptical shape of the predetermined volume model by an error of corresponding magnitude. This deviation can likewise be used in the computation of the correction addition d(k) for example in the case of the above-described Newton method.

With respect to the division of the total projection surface into the described partial surfaces, the method according to one embodiment is very flexible. It is even possible to recreate curved, oval or saddle-shaped detectors in a simple manner by planar partial surfaces and the volume model, which on the basis of projections that were obtained with such detectors, can likewise be optimized iteratively in the described manner by the correction vectors and matched to the detector form, without the detector form having to be previously known at all.

It is likewise possible for two or more physically separate detectors to be used (i.e., the projection surface is thus made up of the separate detector surfaces of two or more detectors). Each of the detector surfaces can be recreated, for example, by a partial surface. The (virtual) displacement of the partial surfaces by the correction vectors then also simulates a relative movement of the detector surfaces owing to a mechanical deformation of their mechanical suspension.

However, also provided is preferably a division into a plurality of partial surfaces within a closed detector surface. As a result, in addition to the relatively low deformation of the detector itself, the non-rigid movement of the body volume, that is to say its deformation, is then also effectively compensated for.

A further embodiment of the method also takes into account the special case that the body or the projection surface carries out an actual rigid movement, that is to say either all volume elements or all radiation sensors effect the same translational or linear movement. In order that not every correction vector of the partial surfaces needs to be matched correspondingly identically in a complicated manner in one or more iteration steps to compensate for the rigid movement, the development provides that for at least one projection angle, at least one further correction vector is additionally ascertained for a source position of the radiation source and/or for an object position of the body volume and the volume model is computed therewith. As a result, the rigid movement can be compensated for by matching a single displacement vector, as a result of which an iterative optimization can converge particularly quickly.

For the optimization method to converge quickly, that is to say so that only a few iteration steps and thus a few computations are necessary for generating the volume model, it is also possible to make provision for a specific initialization of the correction vectors. One advantageous development of the method in this context makes provision for the correction vectors to be set for at least one of the projection angles for the initialization of the associated correction vectors as if the projection surface were composed of structurally fixedly connected partial surfaces. In other words, the projection surface is considered to be a rigid surface, such that no movements of the partial surfaces with respect to one another can occur due to corresponding values of the correction vectors. That is to say, as is known per se from the prior art, for example only one correction is carried out by the detector position vectors U and V. The advantage of this embodiment is that a first iteration of the computation of the volume model is possible using the Feldkamp reconstruction. This may not be consistent and initially provides a poor, yet object-related volume model. However, this initial volume model can then be used for a first correction of the values of the correction vectors, this time independently for each correction vector.

If the already described a priori knowledge relating to the shape and/or composition of the body volume and/or the sensor positions inside the projection surface is known, this can of course also be incorporated during the initialization of the correction vectors by way of fixing corresponding values.

The method according to one embodiment is suitable in principle for operating each radiation-based tomography system, for example a positron emission tomography scanner (PET), a magnetic resonance tomography scanner (MRT) or an X-ray tomography scanner.

Embodiments accordingly also include a tomography system having a sensor device which includes a plurality of radiation sensors that together form a projection surface. The sensor device can also include, for example, a single detector, for example a flat detector, or a plurality of detectors, as is the case for example in a biplanar system.

The tomography system furthermore has a projection device, designed to move the sensor device, that is to say the detector or the detectors, around a body volume along a planned movement trajectory, that is to say for example about a patient, and in the process to generate in each case a projection from different projection angles. To this end, a radiation source, that is to say for example an X-ray source, is used to generate radiation, the beams of which are projected through the body volume onto the projection surface. The projection device can include, for example, a C-arm that carries both the sensor device and the radiation source.

Also part of the tomography system is finally an image generation device, that is to say for example a computing system, which is designed to receive a pixel value during each projection from each radiation sensor, that is to say each recording of the body volume. The pixel values of each individual recording form, in a manner known per se, a 2D image data set. The image generation device then generates the described volume model of the body volume from all the projections. Here, the image generation device carries out an embodiment of the method.

The tomography system according to one embodiment is preferably designed as an X-ray-based computed tomography scanner, that is to say the radiation source includes an X-ray source.

So as to also develop an existing tomography system such that the system is made suitable for carrying out an embodiment of the method, one embodiment also includes a computer program product, that is to say program code, which is stored on at least one storage medium. This program product is designed to carry out, upon execution by a processor device of the tomography system, an embodiment of the method.

DETAILED DESCRIPTION

The exemplary embodiments explained below are preferred embodiments. In the exemplary embodiments, however, the described components of the embodiments in each case represent individual features that should be regarded independently of one another, and which in each case also further develop the invention independently from one another and thus should be considered, even individually or in another combination than the one shown, as being a constituent part of the invention. Furthermore, the described embodiments can also be supplemented by further ones of the already described features.

Figure 1:
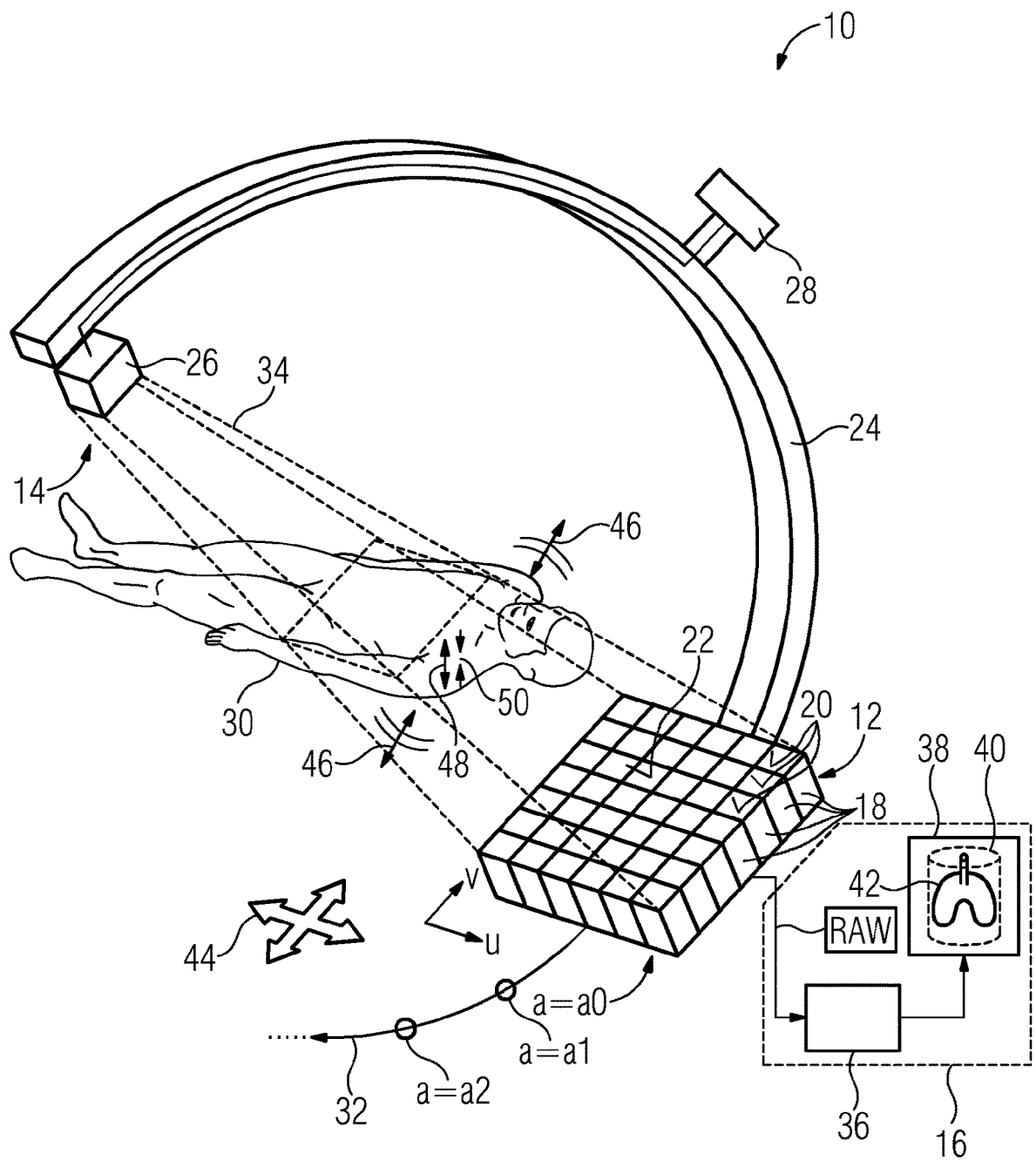
FIG. 1 shows a schematic illustration of an embodiment of the tomography system.

FIG. 1 shows a tomography system 10, which can be for example an X-ray C-arm system. The tomography system 10 can include a sensor device 12, a projection device 14 and an image generation device 16.

The sensor device 12 can include a detector having a plurality of radiation sensors 18, of which only some have reference signs in FIG. 1 for the sake of clarity. Sensor entry surfaces 20 of the individual radiation sensors 18 together form a projection surface 22, that is to say the detector surface that is sensitive overall for a specific radiation. Each individual sensor entry surface 20 forms one pixel of the projection surface 22. The detector can be, for example, a flat detector. In this case, the projection surface 22 is planar.

The projection device 14 can have a carrier element 24, for example a C-arm, which can carry the sensor device 12 and a radiation source 26 of the projection device. The radiation source 26 can be, for example, an X-ray source. A control device 28 can be used to carry out a movement of the carrier device 24 with the sensor device 12 and the radiation source 26 about a body 30. The body 30 can be, for example, a patient to be examined. The body 30 represents a body volume to be examined.

The control device 28 can here move the sensor device 12 along a specified trajectory 32 in a manner known per se and activate the radiation source 26 at specific recording points, which are defined by a projection angle a with respect to the body 30. In FIG. 1, for example, spatial positions of the sensor device 12 for projection angles $a_0$, $a_1$, $a_2$ are indicated. Upon activation of the radiation source 26, the radiation source generates a beam fan or a cone beam 34 from the radiation. The radiation penetrates the body 30 and reaches the projection surface 22. The individual radiation sensors 18 then detect the radiation amount and/or radiation intensity that has penetrated their respective sensor surface 20 and generate a corresponding pixel value. The set of the pixel values is transmitted to the image generation device 16 as raw data RAW. Raw data RAW in this case is understood to mean the pixel values of the radiation sensors 18 for all projection angles a.

The image generation device 16 can include an image processor 36 and a display device 38. The image processor 36 can include, for example, one or more computers. The display device 38 can include, for example, a screen. The image processor 36 calculates a volume model 40 of the transilluminated region of the body 30 from all pixel values, that is to say from the raw data RAW. The volume model 40 can here recreate the shape and position of internal organs 42 of the body 30, such as for example a patient's lung.

During the computation of the volume model 40, the image processor 36 takes into account that, for example, the carrier device 24 can deform, owing to its own weight and the weight of the radiation source 26 and the sensor device 12, in dependence on the assumed projection angle a, and therefore the projection surface 22 carries out a relative movement 44 with respect to the radiation source 26 between the individual recordings (i.e., upon assuming the projection angles $a_1$, $a_2$, $a_3$ and the further projection angles). The relative movement 44 causes the sensor device 12 to be displaced with respect to the radiation source 26, for a given projection angle a, in a direction u and a direction v, if the actual position is compared to the position that is provided according to the construction plan of the tomography system 10.

The image processor 36 also takes into account that the body 30 may change its position owing to a translational movement 46 in the tomography system 10 such that the object position of the body 30 within the tomography system 10 changes between the projection angles a. The image processor 36 also takes into account that the organs 42 are displaced with respect to one another due to a non-rigid movement, for example a breathing movement of the patient, and change their shapes, such that the body volume may undergo, for example, an expansion 48 or a compression 50. However, in the image processor 36, this does not lead to the volume model 40 imaging the organs 42 without sharpness.

Figure 2:
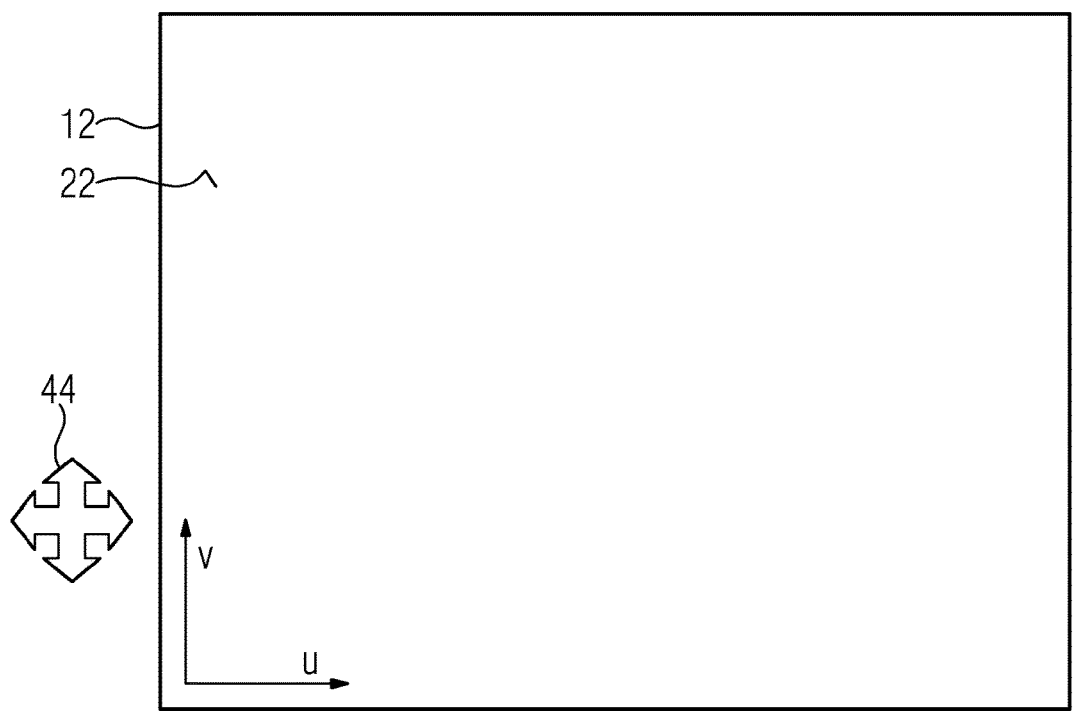
FIG. 2 shows a sketch for illustrating an example rigid movement of a projection surface of the tomography system in FIG. 1.

An abstraction of the representation of the tomography system 10 to the features that are essential for the following explanations is effected in FIG. 2 to illustrate the method carried out by the image processor 36 for compensating the movement and deformation during the generation of the volume model 40.

FIG. 2 shows the projection surface 22 from the view of the radiation source 26. Owing to the relative movement 44 of the sensor device 12 with respect to the radiation source 26, the projection surface 22 changes position with respect to the radiation source 26 between individual projections at the various projection angles a along a direction vector U and a direction vector V. This rigid movement of the projection surface 22 can be compensated for according to the prior art by corresponding calibration methods or iterative image optimization methods. It is not possible, on the other hand, for the expansion 48 and compression 50 of the body volume of the body 30 to be compensated in this way.

Figure 3:
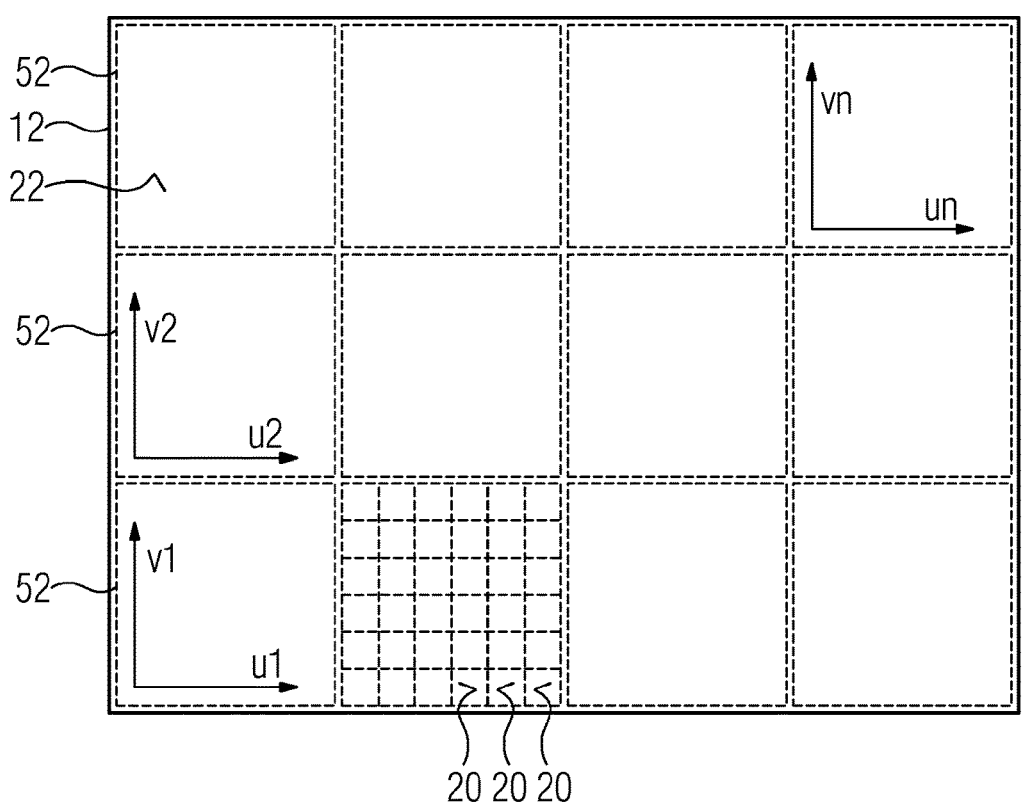
FIG. 3 shows a sketch relating to the example division into partial surfaces of the projection surface of FIG. 2.

For this reason, the image processor 36 carries out a division of the projection surface 22, illustrated in FIG. 3, into partial surfaces 52, of which only some have a reference sign in FIG. 3 for reasons of clarity. Each partial surface 52 can have, for example, the shape of a tile or a square. Each partial surface 52 can here include a plurality of pixels, that is to say a plurality of sensor entry surfaces 20, as is illustrated in FIG. 3 for a partial surface. The image processor 36 assumes that each partial surface 52 can move independently of the other partial surfaces 52 during the movement along the trajectory 32. In other words, it is assumed for each partial surface 52 at a given projection angle a that the partial surface has moved by a distance $u_1$, $u_2, \ldots, u_n$ along the direction vector u and accordingly by a distance $v_1, v_2, \ldots, v_n$ along the movement direction v. Overall, in the example shown, the projection surface 22 is thus divided into n partial surfaces, wherein in FIG. 3 n=12. The distances $u_1$, $u_2$ to $u_n$, $v_1$, $v_2$ to $v_n$ form degrees of freedom in the optimization of the volume model 40 which can be matched, for example, in a recursive method in steps so that the expansion 48 and compression 50 of the transilluminated body volume of the body 30 are also compensated for during the computation of the volume model such that the organs 42 are imaged sharply in the volume model. The vectors $u_1$, $u_2$ to $u_n$ and $v_1$, $v_2$ to $v_n$ represent correction vectors, wherein $u_1, u_2, \ldots, u_n$ and $v_1, v_2$ to $v_n$ are preferably in each case a three-dimensional vector. The vectors can also represent the absolute positions of the partial surfaces 52.

Figure 4:
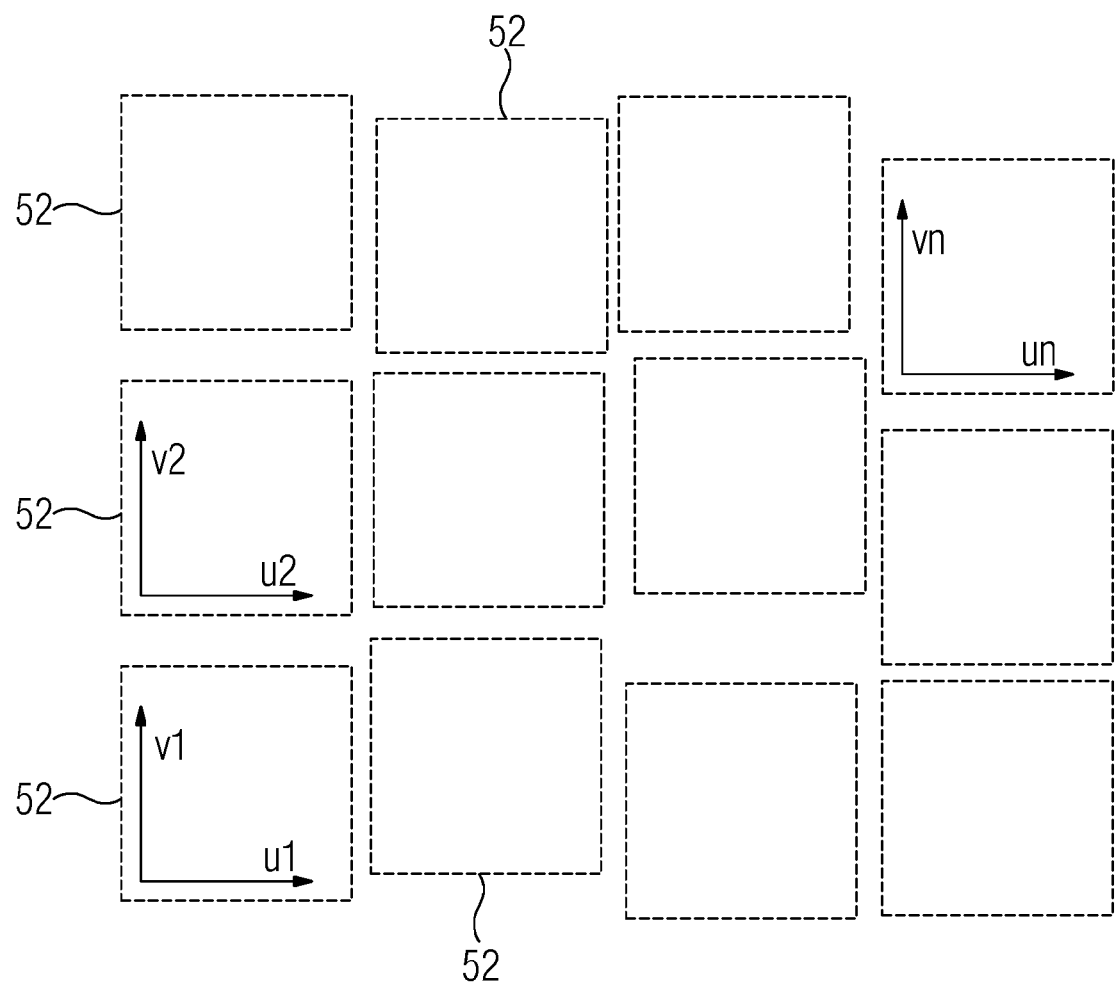
FIG. 4 shows a sketch for illustrating the virtual deformation of the projection surface in the case of the compensation according to one embodiment of a non-rigid movement of a body volume.

FIG. 4 illustrates how, for compensating the non-rigid movement of the body 30, for a given projection angle a, the partial surfaces 52 can have been displaced virtually with respect to one another by corresponding values of the distances $u_1, u_2, \ldots, u_n, v_1, v_2, \ldots, v_n$. In FIG. 4, the surfaces 52 have moved away from one another. Of course this does not mean that the sensor device 12 has actually deformed in this way, that is to say the detector 18 has fallen apart. The change in the positions of the partial surfaces 52 by the stated distances $u_1, u_2, \ldots, u_n, v_1, v_2, \ldots, v_n$ rather corresponds as a result to such raw data RAW as would result if the projection surface 22, as shown in FIG. 3, remained unchanged and the body volume 30 had deformed.

Each distance $u_1, u_2, \ldots, u_n, v_1, v_2, \ldots, v_n$ is here described as a vector. The combination of the vector $u_1$, $v_1$ here describes a positional change by which the corresponding partial surface 52 has to be imagined as being displaced so as to compensate for the non-rigid movement of the body volume in the region of the corresponding partial surface 52. The same is true for the remaining stated distances $u_2, \ldots, u_n, v_2, \ldots, v_n$.

Figure 5:
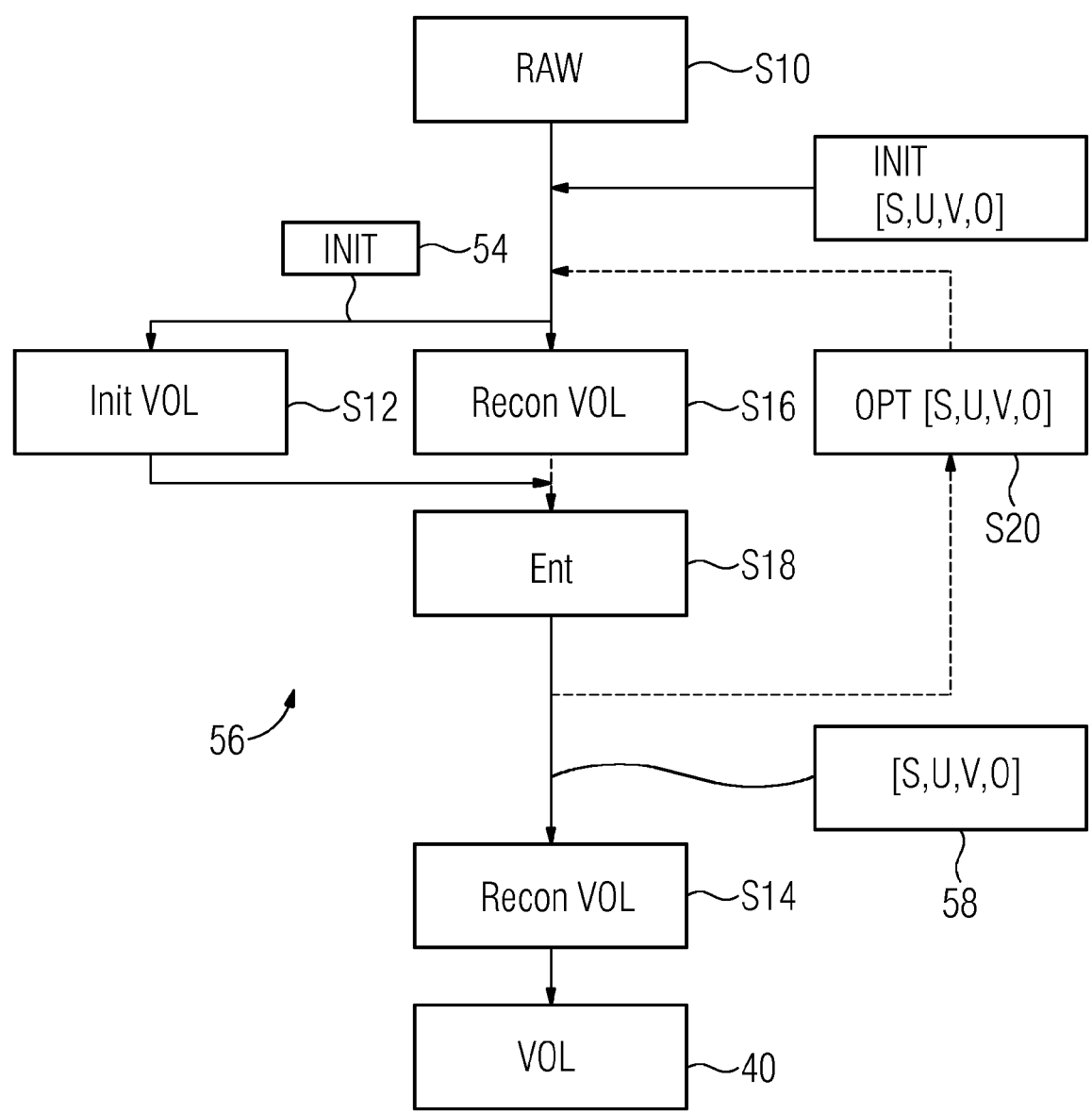
FIG. 5 shows a flowchart relating to one embodiment of the method that can be carried out by the tomography system in FIG. 1.

FIG. 5 illustrates a method which can be carried out by the image processor 36 to obtain the described correction vectors $u_1$, $u_2$ to un and $v_1$, $v_2$ to $v_n$. The image processor 36 can here combine the correction vectors $u_1, u_2, \ldots, u_n$ for a given projection angle a into a matrix $U(a)=[u_1(a), u_2(a), \ldots, u_n(a)]$. Analogously, a matrix $V(a)=[v^1(a), v_2(a), \ldots, v_n(a)]$ can be formed for the movement along the movement direction v at a given projection angle a for the partial surfaces. Provision may additionally be made for a vector s(a) for a movement correction of the radiation source 26 to be provided for the radiation source 26 as well. If a plurality of radiation sources are present, the source positions can likewise be combined into a matrix S(a). A rigid movement of the body 30 can be compensated for either by the matrices S, U, V, or can be defined by an additional object position O(a).

A multi-segment trajectory (i.e., a trajectory for each partial surface 52) is defined across all projection angles a by the matrices U, V. The challenge is now for the correct vector matrices to be determined so as to achieve a consistent geometry of the tomography system 10 and/or motion estimation of the body 30. Consistent in this case is understood to mean that, when computing the volume model 40 from the raw data RAW, pixel values are intended to be made available as input values, as would be obtained in the ideally rigid mechanical components and rigid, motionless body 30.

Figure 6:
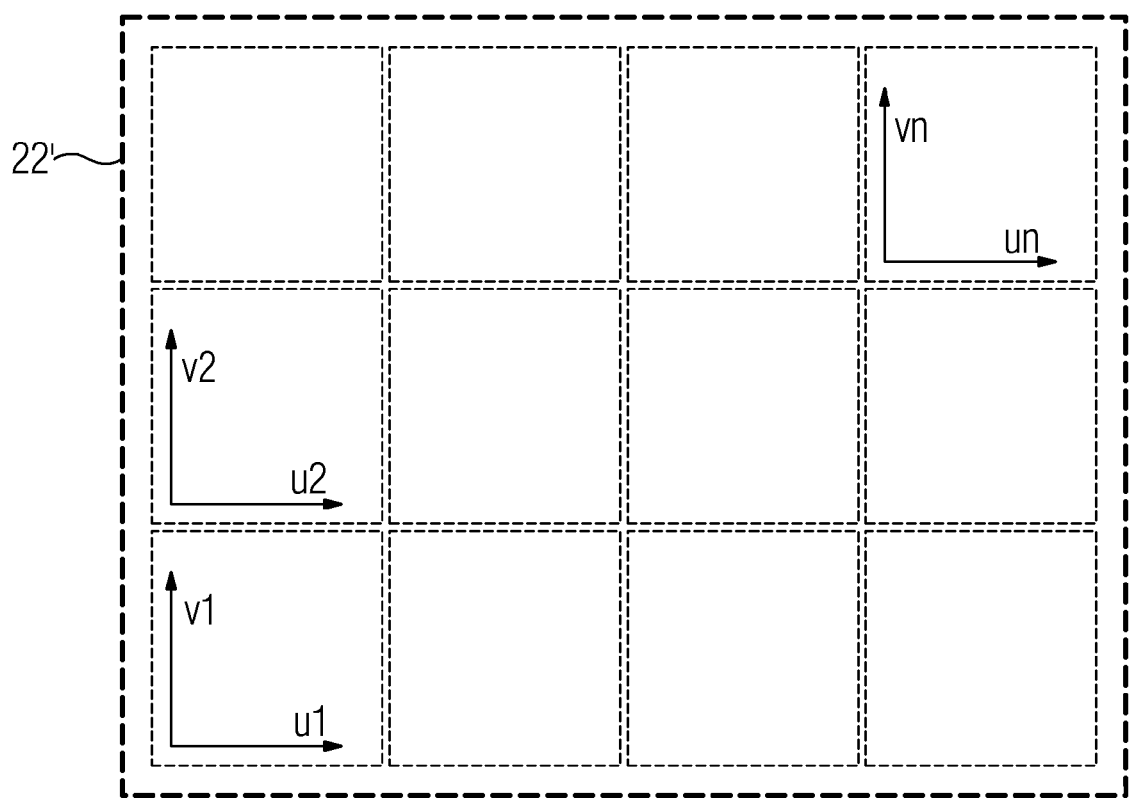
FIG. 6 shows a sketch to illustrate an example initialization phase of the method according to FIG. 5.

A conventional Feldkamp reconstruction for the computation of the volume model 40 is not so easily possible due to the now possible individual and independent (virtual or computational) movement of the partial surfaces 52. However, it is possible for a virtual FDK reconstruction to be carried out as an initialization 54 in act S12 for an initialization after act S10 of receiving the raw data RAW. So as to be able to compute this, the partial surfaces 52, as illustrated in FIG. 6, are initially artificially combined into a rigid detector having a rigid projection surface 22'. As a result, a normal FDK reconstruction can take place. However, this reconstruction is not consistent (i.e., it does not compensate for the relative movements within the tomography system 10). However, instead the reconstruction provides initially a first volume model (Init-VOL), in which the organs 52 are recreated in a relatively blurred form. Even in this phase, the FDK algorithm can receive initial vector matrices (S, O, U, V) as input values for the trajectories of the rigid projection surface 22', the radiation source 26, and the body 30.

These initial vector matrices must then be changed in the course of an iterative optimization 56. This optimization results in new vector matrices 58, in which for all sub-segments of the detector, that is to say the partial surfaces 52, and for all source positions (i.e., the matrix S(a)), the suitable sub-trajectories were computed, by which for example the non-rigid movements 48, 50 are compensated.

As a result, finally in a reconstruction act S14, a motion-compensated reconstructed volume (Recon Vol) can be computed as the volume model 40 (VOL) and be represented for example on the display device 38 as a volume graphic. For the reconstruction of the body volume in act S14 and also during the iterative optimization 46, instead of the FDK algorithm, the optimization is preferably carried out by means of an iterative reconstruction method, in particular ART. To this end, for each iteration in a act S16, the volume model is recomputed based on the actual vector matrix [S, U, V, O]. Subsequently, in act S18, relating to the current volume model, an entropy of the voxel values, for example the absorption coefficients, is computed. The entropy can be computed, for example, as the described entropy value E. Generally, however, a different cost function than the entropy can be additionally or alternatively used. A function should be chosen here, the value of which indicates a deviation from an ideal state, that is to say, for example, the difference with respect to a predetermined volume model.

On the basis of the cost value computed in act S18, a convergence of the reconstruction with respect to the typical movement and misalignment effects can be achieved. The computation of the initial volume in act S12 in this context has the particular advantage that a first entropy value can be computed in the first place, which would not be possible in the case of an initial volume Init VOL having the values O.

In act S20, using a gradient descent method in the described manner, for example, an optimization OPT for the vector matrices U, V and, if appropriate, also for the source position S and the object position O, can now be carried out, so as to change the values thereof within the meaning of an improved volume model. This multi-parameter optimization within the iterative reconstruction 56, for example, with the additional cost function entropy results in the estimation of the sub-trajectories for the individual segments or partial surfaces 52 (i.e., suitable values for U(a), V(a) for all projection angles a). This functionality is then similar in result to a flexible motion compensation, since both the detector, that is to say generally the sensor device 12, and object movement parameters of the body 30 are captured.

It is also possible to integrate act S18 and act S20 in act S16 as a constituent part of an iterative ART algorithm.

So as to be able to carry out the initialization in act S12 in a more targeted manner, that is to say to make available a suitable initial volume Init VOL, it is also possible to use a priori knowledge as the input. For example, a previously ascertained image data set, that is to say a previously ascertained volume model, for example a CT data set, a statistical model, or statements relating to the structure of the tomography system 10 and the appearance and the nature of the body 30 can be used.

Overall, in the embodiments, the non-rigid movement of the examined object is compensated for by the fact that the sensor device 12 is treated as a deformable, non-rigid detector, the partial surfaces 52 of which can move freely with respect to one another. The principle idea here is to define, instead of a global geometry of the total projection surface 22, in this case a local geometry within the projection surface 22 for each individual projection from a projection angle a. The results are the vector matrices for the detector position vectors U(a) and V(a), which describe an optimized position per projection angle a for the partial regions 52 of the detector. In the simplest case, it suffices to determine only new detector positions by the projection matrices U, V to estimate the geometry or movement. However, in that case, a rigid rotation center and only one source must be assumed.

Generally, one embodiment provides a method for generating a digital volume model (40) of a body volume (30), which includes a plurality of volume elements, using a sensor device (12) including a plurality of radiation sensors (18) that together form a projection surface (22). Each radiation sensor (18) represents a pixel (20) of the projection surface (22), and generates a pixel value during a projection, in which the body volume (30) is transilluminated by beams (34). For generating the volume model (40), a plurality of projections from different projection angles (a) are generated by moving the projection surface (22) along a planned movement trajectory (32), and the projections are combined into the volume model (40) by computing for the volume elements in each case an absorption coefficient by a reconstruction of a beam profile of the beams (34) on the basis of the pixel values (RAW) and a respective sensor position of the radiation sensor (18) generating the respective pixel value. The sensor positions for at least one projection angle (a) are corrected using a respective correction vector which is designed to describe a deviation of the position of the projection surface (22) from the planned movement trajectory (32) so that the volume model (40) that is computed on the basis of the corrected sensor positions meets a specified optimization criterion. For the correction of the sensor positions for one or more or all of the projection angles (a), in each case the projection surface (22) is divided into a plurality of partial surfaces (52) and in each case a dedicated correction vector (u1, v1; u2, v2; un, vn) is ascertained relating to the partial surfaces (52) independently of one another.

Overall, the example shows how a simultaneous geometry calibration of the tomography system 10 and a non-rigid motion compensation of the body volume of the body 30 can be achieved on the basis of a multi-parameter image optimization based on a cost function. To this end, the reconstruction is carried out under the assumption of a multi-segment detector for the tomography having an initially unknown geometric arrangement. Another resulting advantage here is that a general trajectory definition can be ascertained also for curved, oval or saddle-shaped detectors, which can then be optimized by the described iterative optimization. The method can also be applied for one or more source systems owing to the vector matrix S(a).

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating a digital volume model of a body volume using a sensor device comprising a plurality of radiation sensors, the method comprising:
   generating a pixel value during a projection with the radiation sensors, in which the body volume is transilluminated by radiation;
   generating the volume model from a plurality of projections from different projection angles, wherein the volume model is computed in dependence on sensor positions of the radiation sensors and the pixel values thereof, and here in each case the sensor positions for at least one projection angle are corrected using at least one correction vector for a rigid motion compensation;
   for correcting the sensor positions for one, more, or all of the projection angles during reconstruction, a projection surface being entry surfaces of a totality of the radiation sensors is divided into a plurality of partial surfaces and at least one dedicated correction vector is used for each of the partial surfaces independently from one another, the correction vectors being spatial displacements of the respective partial surfaces of the projection surface formed by the entry surfaces of the totality of the radiation sensors.

2. The method as claimed in claim 1, wherein voxel values of the volume model are ascertained using an iterative algebraic reconstruction technique, ART.

3. The method as claimed in claim 2, wherein the correction vectors are iteratively optimized and an error quantifier defined by the optimization criterion is iteratively reduced.

4. The method as claimed in claim 3, wherein the radiation sensors are provided by at least two physically separate detectors, and as a result the projection surface comprises spatially separate detector surfaces which are formed by the respective radiation sensors of the detector and each detector surface is described by at least one of the partial surfaces.

5. The method as claimed in claim 3, wherein, within a detector comprising at least part of the radiation sensors, a closed detector surface of which is divided into a plurality of the partial surfaces.

6. The method as claimed in claim 5, wherein for at least one projection angle, at least one further correction vector is additionally ascertained for a source position of the radiation source of the beams, for an object position of the body volume, or for the source position of the radiation source of the beams and for the object position of the body volume, and the volume model is generated therewith.

7. The method as claimed in claim 5, wherein for initializing for at least one of the projection angles the correction vectors are set as obtained from structurally fixedly connected partial surfaces.

8. The method as claimed in claim 5, wherein for initializing for at least one of the projection angles, the correction vectors are set on the basis of a priori knowledge relating to (i) a shape, a composition, or a shape and composition of the body volume, (ii) the sensor positions within the projection surface, or (iii) the shape, the composition, or the shape and the composition of the body volume and the sensor positions within the projection surface.

9. The method as claimed in claim 1, wherein the correction vectors are iteratively optimized where an error quantifier defined by an optimization criterion is iteratively reduced.

10. The method as claimed in claim 9, wherein the optimization criterion comprises that an entropy computed on the basis of voxel values of the volume model is reduced by the corrected sensor positions in comparison with uncorrected sensor positions.

11. The method as claimed in claim 9, wherein the optimization criterion comprises that the volume model owing to the corrected sensor positions deviates less from a specified predetermined volume model of the body volume according to a specified error quantifier than with uncorrected sensor positions.

12. The method as claimed in claim 1, wherein an optimization criterion comprises that the volume model owing to the corrected sensor positions deviates less from a specified predetermined volume model of the body volume according to a specified error quantifier than with uncorrected sensor positions.

13. The method as claimed in claim 1, wherein the radiation sensors are provided by at least two physically separate detectors, and as a result the projection surface comprises spatially separate detector surfaces which are formed by the respective radiation sensors of the detector and each detector surface is described by at least one of the partial surfaces.

14. The method as claimed in claim 1, wherein, within a detector comprising at least part of the radiation sensors, a closed detector surface of which is divided into a plurality of the partial surfaces.

15. The method as claimed in claim 1, wherein for at least one projection angle, at least one further correction vector is additionally ascertained for a source position of the radiation source of the beams, for an object position of the body volume, or for the source position of the radiation source of the beams and for the object position of the body volume, and the volume model is generated therewith.

16. The method as claimed in claim 1, wherein for initializing for at least one of the projection angles the correction vectors are set as obtained from structurally fixedly connected partial surfaces.

17. The method as claimed in claim 1, wherein for initializing for at least one of the projection angles, the correction vectors are set on the basis of a priori knowledge relating to (i) a shape, a composition, or a shape and composition of the body volume, (ii) the sensor positions within the projection surface, or (iii) the shape, the composition, or the shape and the composition of the body volume and the sensor positions within the projection surface.

18. A tomography system comprising:
  a sensor device having a plurality of radiation sensors with entry surfaces that together form a projection surface,
  a projection device designed to move the sensor device around a body volume along a planned movement trajectory and to project, for a plurality of projections from in each case a different projection angle, beams through the body volume onto the projection surface in each case using a radiation source,
  an image generation device configured to receive a pixel value for each projection from each radiation sensor and to generate from all the projections a volume model of the body volume, wherein the image generation device is configured to correct sensor positions for one, more, or all of the projection angles during reconstruction of the volume model where the projection surface is divided into a plurality of partial surfaces and dedicated correction vectors are used for the partial surfaces independently from one another.

19. The tomography system as claimed in claim 18, wherein the projection device has an X-ray source for generating the beams and the tomography system is an X-ray-based computed tomography scanner.

20. A non-transitory computer program product having program code stored on at least one storage medium, which code is designed to carry out, upon execution by a processor device of a tomography system, the code comprising instructions for:
  generating, by reconstruction, a volume model from a plurality of projections from different projection angles, wherein the volume model is computed in dependence on sensor positions of radiation sensors and the pixel values thereof, and here in each case the sensor positions for at least one projection angle are corrected during the reconstruction using at least one correction vector for a rigid motion compensation;
  for correcting the sensor positions for one, more, or all of the projection angles, a projection surface defined as a surface of a totality of the radiation sensors is divided into a plurality of partial surfaces and in each case at least one dedicated correction vector is used for the partial surfaces independently from one another.

* * * * *